United States Patent [19]

Nakamura et al.

[11] Patent Number: 4,990,451
[45] Date of Patent: Feb. 5, 1991

[54] PROCESS FOR THE PREPARATION OF INULASE

[75] Inventors: Toyohiko Nakamura, Miyazaki; Toshio Takizawa, Kanagawa; Yoshihiro Kamo, Kanagawa; Hidemasa Hidaka, Kanagawa, all of Japan

[73] Assignee: Meiji Seika Kaisha, Ltd., Tokyo, Japan

[21] Appl. No.: 467,285

[22] Filed: Jan. 18, 1990

Related U.S. Application Data

[63] Continuation of Ser. No. 23,323, Mar. 9, 1987, abandoned.

[30] Foreign Application Priority Data

Mar. 7, 1986 [JP] Japan .................................. 61-48575

[51] Int. Cl.$^5$ .............................................. C12N 9/26
[52] U.S. Cl. .................................... 435/201; 435/183; 435/254; 435/917
[58] Field of Search ............... 435/183, 254, 200, 201, 435/193, 816, 917

[56] References Cited

U.S. PATENT DOCUMENTS 3,919,049 11/1975 Kiuchi et al. ..................... 195/66 R

FOREIGN PATENT DOCUMENTS 043169 1/1982 European Pat. Off. .

OTHER PUBLICATIONS

Studies on Microbial Inulase. Part IV, Crystallization and General Properties of an Extracellular Inulase (P-III)ZI=5 Aspergillus sp. Nakamura, T. et al., Nippon Nogei Kagaku Kaishi, 52(4), 159-66, 1978.

*Primary Examiner*—Carolyn S. Elmore
*Attorney, Agent, or Firm*—Sughrue, Mion, Zinn, Macpeak & Zinn

[57] ABSTRACT

A process for preparing endoinulase by cultivating a microorganism belonging to the genus Aspergillus and capable of producing inulase and recovering the inulase produced and accumulated in the culture medium by organic solvent precipitation, wherein inulase having a high exo activity is first precipitated at a low concentration of a water-soluble organic solvent and is removed, and then inulase having a high endo activity is precipitated at a high concentration of the water-soluble organic solvent and is recovered.

4 Claims, No Drawings

PROCESS FOR THE PREPARATION OF INULASE

This is a Continuation of Application No. 07/023,323 filed Mar. 9, 1987.

FIELD OF THE INVENTION

This invention relates to a process for preparing an enzyme which acts on inulin or a plant containing inulin, e.g., artichokes (*Helianthus tuberosus* L.), chicory, etc., to produce fructo-oligosaccharides with industrial advantages.

BACKGROUND OF THE INVENTION

The terminology ("fructo-oligosaccharide") as used herein means oligosaccharides represented by formula (I) shown below, in which at least two fructose residues are bonded through a $\beta$-1,2-linkage to form a main chain.

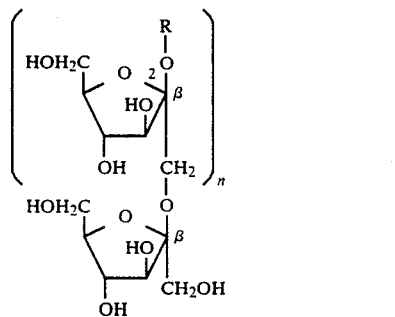

(I)

wherein R represents a hydrogen atom or a glucose residue; and n represents an integer of from 1 to 5.

Fructo-oligosaccharides of formula (I) wherein R is a hydrogen atom include inulobiose, inulotriose, inulotetraose, inulopentaose, etc. These fructo-oligosaccharides are known to be naturally present in artichokes, cluster-amaryllis (*Lycoris radiata* Herb.), etc. and can be prepared by hydrolysis of inulin or lycoricine with an acid or an enzyme.

The fructo-oligosaccharides of formula (I) wherein R is a glucose residue include 1-kestose, nystose, fructosylnystose, etc. These oligosaccharides are also known to be present in artichokes, onions, leeks (*Allium odorum*), etc. They can be synthesized by fructose inversion of sucrose by the action of invertase. Industrial production of fructo-oligosaccharides by utilizing the action of invertase is known in the art.

Although fructo-oligosaccharides are less sweet than sucrose, they have excellent characteristics which are not associated with sucrose. One of the characteristics is their excellent effect on the growth of intestinal flora, particularly Bifidobacterium. That is, fructo-oligosaccharides ingested are not susceptible to decomposition by human or animal digestive enzymes and easily reach the large intensine, where they are selectively utilized by Bifidobacterium to accelerate the growth of Bifidobacterium. Studies have demonstrated that keeping the number of Bifidobacterium above a certain level in the intestine is important for health maintenance. In fact, it has been reported that Bifidobacterium increased upon ingestion of fructo-oligosaccharides brings about constipation or diarrhea relief and a reduction of intestinal putrefaction caused by noxious bacteria. Therefore, when fructo-oligosaccharides are given to animals, they contribute to the promotion of growth and improvement of feed efficiency. Further, administration of fructo-oligosaccharides produces physiological effects, such as improvement in lipemia, reduction in cholesterol level in the serum, reduction in blood pressure, and the like. These effects are considered to arise due to the actions upon the intestinal flora.

In addition, fructo-oligosaccharides have been reported to hardly cause dental caries. Dental caries is attributed to *Streptococcus mutans*, a lactic acid bacteria in the oral cavity. The mechanism of the development of dental caries is as follows. *Streptococcus mutans* secretes dextran synthetase which acts on sucrose, a substrate, to synthesize dextran. The dextran sticks to the surfaces of teeth to form dental plaques thereon, in which *Streptococcus mutans* ferments fermentable saccharides anaerobically to produce lactic acid thereby to cause decalcification of the dental enamel. When fructo-oligosaccharides are involved in this mechanism, they do not serve as substrates either for dextran synthesis due to dextran synthetase secreted from *Streptococcus mutans* or for anaerobical fermentation of *Streptococcus mutans*. The fact that the fructo-oligosaccharides hardly cause dental caries has been demonstrated in animal experiments.

As described above, fructo-oligosaccharides are very useful, and establishment or improvement of an industrial process for preparing them is considered greatly worthwhile.

It is possible to produce fructo-oligosaccharides from inulin or a plant containing inulin by hydrolysis using acids or enzymes as mentioned above. Inulin is relatively labile to acids, and its hydrolysis is generally carried out in the laboratory using oxalic acid. However, oxalic acid is not favorable for use in industrial production of food materials because it is highly toxic and low yields are attained therewith. As a result, a process comprising hydrolyzing inulin by the action of inulase has been employed. Known inulase includes those of plant origin and those of microorganism origin. In general, the former has low activity, and the latter has high exo activity that is suitable for the production of fructose but unsuitable for the production of oligosaccharides. Therefore, production of inulase of high endo activity suitable for the production of oligosaccharides requires removal of inulase of high exo activity from a culture or powder of a microorganism containing both types of inulase and fractionation and recovery of inulase having high endo activity.

Conventionally known processes for obtaining inulase having high endo activity include adsorption and desorption by column chromatography using organic ion-exchangers, e.g., DEAE-Sephadex A-50; fractionation and purification by gel-filtration column chromatography using Sephadex G-50, etc.; and combinations thereof. These techniques are not suitable, however, for obtaining inulase for use in the mass production of foods at low cost, although they are excellent when applied for the purpose of obtaining highly purified inulase for use in, for example, laboratories. Hence, it has been desired to develop a technique for preparing inulase of high endo activity on an industrial scale.

SUMMARY OF THE INVENTION

Accordingly, one object of this invention is to provide a process for preparing inulase having high endo activity with industrial advantages.

It has been found in this invention that there is a difference between exoinulase and endoinulase in terms of their behavior in water-soluble organic solvents, such as alcohols, acetone, etc., i.e., there is a difference in concentration in these solvents at which precipitation takes place.

DETAILED DESCRIPTION OF THE INVENTION

Any of mciroorganisms belonging to the genus Aspergillus and capable of producing inulase can be used in the present invention. Among these microorganisms, *Aspergillus niger* is preferred, and *A. niger* M(T) 114 strain is particularly preferred.

The microbiological properties of *A. niger* M(T) 114 strain are described below.

I. Growth on Various Media (28° C., 7 day-cultivation)

(1) Czapek's Medium

The growth rate is as low as 2 to 3 mm,/day. Velvet-like mycelia are formed. The mycelium is white in the initial stage and turns to yellow at about the beginning of conidium formation from the central portion. The conidia are formed satisfactorily with black heads. The reverse side of the conidial head is white in the initial stage but turns to yellow after the start of conidiospore formation.

(2) Malt Agar Medium

The growth rate is as high as 7 to 8 mm/day. Velvet-like mycelia are formed and conidia are formed from the central portion. Conidium formation is satisfactory. Differing from the case of Czapek's medium, the mycelium remains white. The heads of the conidia are black with their reverse side being white.

II. Physiological Properties (1) Growth pH

Capable of growth in a pH range of from 2.0 to 9.0, with the optimal range being from 4.5 to 6.5.

(2) Growth Temperature

Capable of growth in a pH temperature range of from 5° to 40° C., with the optimal range being from 25° to 30° C.

III. Form and Characteristics

The conidiophores arise from the basal hypha layer, reaching a height of from 2 to 3 mm at the longest. The conidial head has a diameter of about 400 μm, radiates from the center, and is black. The apical sac has a spherical form having a diameter of about 50 μm. The metula is brown and measures about 20×5 μm. The phialide measures about 10×3 μm. The conidiospore is brown and has a spherical form having a diameter of about 3 μm. The wall surface has an irregular roughness.

The bacterial strain of interest having the above-described microbiological properties was identified as *Aspergillus niger* according to S. Udagawa, K. Tsubaki, et al., *Kinrui Zukan*, Vols. I and II, Kodansha (1977). This strain has been deposited in Agency of Fermentation Research Institute, Japan (FERM BP-1289).

A process for producing and recovering inulase of high endo activity by using *A. niger* M(T) 114 is described below.

The medium to be used for cultivation comprises carbon sources, nitrogen sources, inorganic salts, and other nutrient sources that can be utilized by the strain. The carbon sources include glucose, fructose, galactose, xylose, soluble starch, dextrin, lactose, sucrose, maltose, etc. The nitrogen sources include organic materials, e.g., peptone, corn steep liquor, meat extract, soy bean lees, wheat bran, etc., and inorganic compounds, e.g., ammonium salts, nitric acid salts, etc. The inorganic salts include phosphates, sulfates, hydrochlorides, and the like. Further, addition of various vitamins, yeast extract, and the like is effective to ensure growth of the cultures.

Prior to cultivation, it is preferable that a seed culture obtained by precultivation is added to a production medium. Cultivation is usually carried out at a temperature of from 20° to 40° C., and preferably from 25° to 30° C., for a period of from 2 to 7 days. During the cultivation, it is preferable to supply sufficient oxygen to accelerate growth by aeration with stirring or shaking.

After completion of the cultivation, since the enzyme produced is liberated predominantly into the culture medium, the culture medium may be subjected as such to purification steps without requiring rupture and extraction of the microbial cells. That is, the microbial cells and any solid matter are removed from the culture by filtration or centrifugation, and the filtrate or supernatant liquor is concentrated by ultrafiltration or concentration under reduced pressure while suppressing deactivation of the enzyme. An organic solvent easily soluble in water, e.g., lower alcohols such as ethanol, n-propyl alcohol and isopropyl alcohol, acetone, acetonitrile, dioxane, etc., is added to the concentrate. Exoinulase is first precipitated and removed at a low concentration of the organic solvent, and then endoinulase is precipitated and recovered at an elevated organic solvent concentration.

In the case of using ethanol, for example, as the organic solvent, when it is added to a concentration of 60% by volume, an inulase fraction having high exo activity is first precipitated. After removing this fraction by filtration or centrifugation, ethanol is further added to the mother liquor up to a concentration of 70% by volume, thereby to precipitate inulase having high endo activity, which is then recovered by centrifugation or the like procedure, followed by drying under reduced pressure to obtain a powder. The precipitation is preferably effected at low temperatures, more preferably 10° C. or lower.

The activity of exoinulase can be assayed by reacting the enzyme with sucrose in an acetic acid buffer (pH=5.0) (final concentration: 0.25% by weight) and determining the reducing sugar resulting from the reaction by a Somogyi-Nelson's method. The enzymatic reaction is carried out at 40° C., and the enzymatic activity which produces 2 μmol of a reducing sugar per minute under such a reaction condition is taken as one unit.

The activity of endoinulase can be assayed by reacting the enzyme with inulin in an acetic acid buffer (pH=5.O) (final concentration: 0.25% by weight) and determining the reducing sugar resulting from the reaction by a Somogyi-Nelson's method. The enzymatic reaction is carried out at 40° C., and the enzymatic activity which produces 1 μmol of a reducing sugar per minute under such a reaction condition is taken as one unit.

The endo activity of the culture or powder is evaluated by the ratio of the thus determined endoinulase activity to exoinulase activity (I/S ratio). When fructooligosaccharides are prepared by the action of inulase on inulin or a plant containing inulin, the inulase to be used preferably has an I/S ratio of at least 10. Most of the enzymes originated from microorganisms which are currently available have an I/S ratio of 3 or less, and are, therefore unsuitable for preparing fructo-oligosaccharides unless they are subjected to fractionation.

The concentrations of various water-soluble organic solvents at which exoinulase or endoinulase is precipitated, the recoveries of endoinulase, and the I/S ratios of recovered fractions are summarized in Table 1 below. The enzyme liquid prior to the solvent precipitation according to the present invention had an I/S ratio of 4.4.

TABLE 1

| Organic Solvent | Conc. for Precipitation of Exoinulase (v/v %) | Conc. for Precipitation of Endoinulase (v/v %) | Recovery (v/v %) | I/S Ratio |
|---|---|---|---|---|
| Methanol | 70 | 80 | 77 | 136.6 (31)* |
| Ethanol | 60 | 70 | 79 | 62.2 (14)* |
| Isopropyl Alcohol | 50 | 60 | 74 | 34.4 (7.8) |
| Acetone | 50 | 60 | 85 | 23.2 (5.3) |

Note: *Values in the parentheses indicate factors of increase based on the initial I/S ratio (4.4).

As can be seen from Table 1, the process according to the present invention brings about marked improvement in the I/S ratio and satisfactory recoveries. When the thus recovered inulase exhibiting high endo activity is actually acted on inulin or plants containing inulin, saccharification liquids having a fructo-oligosaccharide content as high as 80% by volume or sometimes even more can be obtained.

This invention will now be illustrated in greater detail with reference to the following examples, but it should be understood that the present invention is not limited thereto. In these examples, all the percents are given by weight unless otherwise indicated.

EXAMPLE 1

One platinum loopful of *Aspergillus niger* M(T) 114 (FERM BP-1289) from a slant culture was inoculated to a barley medium and cultured at 28° C. for 10 days. The barley medium was prepared by swelling 100 g of pressed barley grains with 55 ml of a solution comprising 0.5% of glucose, 1.0% of lactose, 0.5% of meat extract, 0.10% of ammonium sulfate, 0.1% of monopotassium phosphate, 0.05% of potassium chloride, 0.05% of magnesium sulfate heptahydrate, and 0.001% of ferrous sulfate heptahydrate, followed by sterilization in an autoclave.

After the culturing, 200 ml of sterilized water was added to the culture. The barley grains were loosened with a loop, and solids were removed by filtering through gauze to obtain a suspension as a seed culture.

One milliliter of the resulting seed culture was inoculated to 30 ml of a production medium comprising 3% of fructose, 2% of corn steep liquor, 1.2% of ammonium phosphate, 0.05% of magnesium sulfate heptahydrate, 0.07% of potassium chloride, 0.001% of ferrous sulfate heptahydrate, and 1.0% of calcium carbonate, and shake-cultured at 30° C. for 6 days.

The resulting culture was filtered with a filter aid, and the filtrate was concentrated by the use of an ultrafilter ("HIP10", hollow fiber type, manufactured by Amicon Co.).

To the concentrate was added ethanol previously cooled in a freezer (−20° C.) to a concentration of 60% by volume. The precipitate thus formed was removed by centrifugal separation (3000 rpm, 10 minutes) at a low temperature. The supernatant liquor was recovered, and an additional amount of ethanol was added thereto to a concentration of 70% by volume. The precipitate formed was separated by centrifugation (3000 rpm, 10 minutes) at a low temperature and dried under reduced pressure to obtain an inulase powder having a high endo activity. The recovery of the active fraction was 79% by volume, and the powder had an I/S ratio of 62.2, that was greater than the initial I/S ratio, 4.4, by a factor of 14.

EXAMPLE 2

To the concentrate obtained in Example 1 was added methanol previously cooled in a freezer (−20° C.) to a concentration of 70% by volume under ice-cooling. The formed precipitate was removed by centrifugation (3000 rpm, 10 minutes), and methanol was further added to the recovered supernatant liquor to a concentration of 80% by volume. The precipitate thus formed was recovered by centrifugation (3000 rpm, 10 minutes) at a low temperature and dried under reduced pressure to obtain an inulase powder having a high endo activity. The recovery of the active fraction was 77% by volume, and the powder had an I/S ratio of 136.6, that was greater than that of the starting concentrate by a factor of 31.

As described above, the present invention makes it possible to effectively and selectively recover an inulase fraction exhibiting high endo activity, which is suitable for the production of fructo-oligosaccharides, from inulase originated from microorganisms belonging to the genus Aspergillus. Therefore, the present invention obviously makes an important contribution to the industrial production of fructo-oligosaccharides.

While the invention has been described in detail and with reference to specific embodiments thereof, it will be apparent to one skilled in the art that various changes and modifications can be made therein without departing from the spirit and scope thereof.

What is claimed is:

1. A process for preparing endoinulase, consisting of cultivating *Aspergillus niger* M(T) 114 (FERM BP-1289) and capable of producing inulase, and recovering the inulase produced and accumulated in the culture medium by organic solvent precipitation, wherein inulase having a high exo activity is first precipitated at a low concentration of a water-soluble organic solvent and removed, and then inulase having a high endo activity is precipitated at a high concentration of the water-soluble organic solvent and recovered.

2. The process as in claim 1, wherein the water-soluble organic solvent is methanol and the low concentration thereof is 70 (v/v%) and the high concentration thereof is 80 (v/v%).

3. The process of claim 1, wherein the water-soluble organic solvent is isopropyl alcohol and the low concentration thereof is 50 (v/v%) and the high concentration thereof is 60 (v/v%).

4. The process of claim 1, wherein the water-soluble organic solvent is acetone and the low concentration thereof is 50 (v/v%) and the high concentration thereof is 60 (v/v%).

* * * * *